United States Patent [19]

Yamabe et al.

[11] 4,412,054

[45] Oct. 25, 1983

[54] ANTITHROMBOGENIC POLYURETHANES BASED ON FLUORINATED PREPOLYMERS

[75] Inventors: Masaaki Yamabe, Machida; Masao Kato; Teruo Takakura, both of Yokohama, all of Japan

[73] Assignee: Asahi Glass Company Ltd., Tokyo, Japan

[21] Appl. No.: 408,936

[22] Filed: Aug. 17, 1982

[30] Foreign Application Priority Data

Sep. 4, 1981 [JP] Japan .............................. 56-138640

[51] Int. Cl.$^3$ ..................... C08G 18/77; C08G 18/48; C08G 18/50
[52] U.S. Cl. ........................ 528/70; 528/28; 528/85; 528/904
[58] Field of Search .......................................... 528/70

[56] References Cited

U.S. PATENT DOCUMENTS

| 3,429,856 | 2/1969 | Hoeschele | 528/70 |
| 3,475,384 | 10/1969 | Trischler | 528/70 |
| 3,642,705 | 2/1972 | Zollinger | 528/70 |
| 3,671,497 | 6/1972 | Stump et al. | 528/70 |
| 3,755,265 | 8/1973 | Stump et al. | 528/70 |
| 4,098,742 | 7/1978 | Mueller | 528/70 |

OTHER PUBLICATIONS

Hollander et al., Polymer Science Part A-1, vol. 5, 2757-2767 (1967).

*Primary Examiner*—H. S. Cockeram
*Attorney, Agent, or Firm*—Oblon, Fisher, Spivak, McClelland & Maier

[57] ABSTRACT

An antithrombogenic material is composed of a fluorine-containing block polymer obtained by the polyaddition or polycondensation of a prepolymer with a chain extender, said prepolymer being a diisocyanate prepolymer represented by the formula

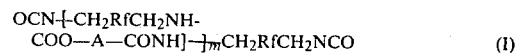
(I)

wherein Rf is a perfluoroalkylene or perfluoroxyalkylene group having from 1 to 20 carbon atoms and containing from 0 to 10 ether linkages, A is a divalent organic group containing an oxygen atom in its main chain and m is from 1 to 3, or a dicarbamate prepolymer obtained by reacting the diisocyanate prepolymer with a lower alcohol.

3 Claims, No Drawings

ANTITHROMBOGENIC POLYURETHANES BASED ON FLUORINATED PREPOLYMERS

BACKGROUND OF THE INVENTION

1. Field of the Invention

The present invention relates to antithrombogenic materials which are useful as biochemical materials for medical appliances such as artificial organs, artificial grafts or blood transfusion apparatus, which are used in direct contact with blood.

2. Description of the Prior Art

Heretofore, various polymer materials have been proposed as such antithrombogenic materials, and some of them are practically used. However, the conventional materials have some drawbacks such that the antithrombogenicity is inadequate, the durability is poor, the mechanical properties are poor or the processability is not good.

SUMMARY OF THE INVENTION

The present inventors have conducted an extensive research to overcome the above difficulties and as a result, have found that a fluorine-containing block polymer obtained by reacting a certain specific prepolymer with a chain extender has superior antithrombogenicity as well as superior durability, mechanical properties or processability and thus is extremely useful as an antithrombogenic material. The present invention has been accomplished based on this discovery.

An antithrombogenic material which is composed of a fluorine-containing block polymer obtained by the polyaddition or polycondensation of a prepolymer with a chain extender, said prepolymer being a diisocyanate prepolymer represented by the formula $$OCN{\hbox{---}}[CH_2R_fCH_2NHCOO{\hbox{---}}A{\hbox{---}}CONH]_m{\hbox{---}}CH_2R_fCH_2NCO \quad (I)$$

where Rf is a perfluoroalkylene or perfluoroxyalkylene group having from 1 to 20 carbon atoms and containing from 0 to 10 ether linkages, A is a divalent organic group containing an oxygen atom in its main chain and m is from 1 to 3, or a dicarbamate prepolymer obtained by reacting the diisocyanate prepolymer with a lower alcohol.

DETAILED DESCRIPTION OF THE PREFERRED EMBODIMENTS

In the present invention, it is important that the fluorine-containing block polymer is the one obtained by subjecting a prepolymer having a specific structure to a chain extension. Such a fluorine-containing block polymer has a molecular structure in which fluorine-containing segments and segments represented by A in the above formula are regularly arranged in the main chain. With such a molecular structure, both of the segments in the block polymer form a microphase separated structure, whereby the block polymer exhibits superior antithrombogenicity. Further, by virtue of the fluorine-containing groups, the block polymer has superior durability and bio-compatibility as well as superior mechanical properties, and is readily soluble in a solvent whereby it can readily be applied by coating, thus providing a merit of excellent processability.

Whereas, in a case of a fluorine-containing polymer in which the fluorine-containing segments and the hydrophilic segments are irregularly arranged, such as a graft polymer obtained by the graft polymerization of polytetrafluoroethylene with a hydrophilic monomer, it is difficult to form a microphase separated structure and such a polymer tends to be poor in its antithrombogenicity. Further, in a case of a block polymer which does not contain fluorine, such as a block polymer of a hydrocarbon or siloxane, the durability, processability or mechanical properties tend to be poor, such being undesirable.

The diisocyanate prepolymer used as a starting material of the present invention may be prepared by reacting m+1 mol of a fluorine-containing diisocyanate represented by the formula $OCNCH_2R_fCH_2NCO$ with m mol of a dihydroxyl compound represented by the formula HO—A—H (not only the single compound but also a mixture of such compounds may be used). The dicarbamate prepolymer may be prepared by reacting the diisocyanate prepolymer thus obtained, with a lower alcohol.

In the above formula (I), Rf is a perfluoroalkylene group having from 1 to 20 carbon atoms, preferably from 1 to 10 carbon atoms, and from 0 to 10 ether linkages, preferably from 0 to 4 ether linkages. Specifically, there may be mentioned $-(CF_2)_l-$ (l=1–10), $-CF_2CF_2OCF_2CF_2-$, $-CF_2CF_2O(CF_2)_nOCF_2CF_2-$ (n=1–5), $-CF(CF_3)O(CF_2)_nOCF(CF_3)-$, or $-CF_2CF_2OCF(CF_3)O(CF_2)_nOCF(CF_3)CF_2OCF_2CF_2-$.

In the formula (I), m is from 1 to 3. In the polymer, there may be present polymer units where m is 1 and polymer units where m is 2 or 3 at the same time. However, for the mechanical properties of the polymer, the higher the proportion of the polymer units where m is 1, the better. In the formula (I), A is a divalent organic group, and it is important for the formation of the microphase separated structure with the fluorine-containing segments that the divalent organic group has an oxygen atom on its main chain.

The structure of A may optionally be changed by selecting the dihydroxyl compound of the formula HO—A—H. However, in view of the antithrombogenicity and durability of the block polymer, it is preferred to use, as the dihydroxyl compound, a polyalkylenediol so that A becomes to be an oxyalkylene group having an average molecular weight of from 40 to 10,000, especially from 400 to 4,000. As preferred specific examples of A, there may be mentioned $-(CH_2CH_2O)_p-$ (p=8–70), $-(CH_2CH_2CH_2CH_2O)_q-$ (q=5–42), $-[CH(CH_3)CH_2O]_r-$ (r=6–54), $-(CH_2CH_2O)_a-[CH(CH_3)CH_2O]_b-(CH_2CH_2O)_c-$ (a, c=1–5, b=4–50), or

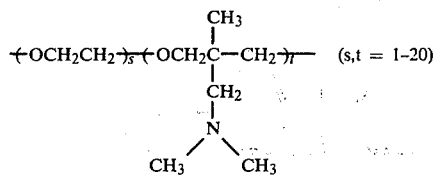

Further, depending upon the particular purpose of the antithrombogenic material, the above polyoxyalkylene diol may partially or wholly be substituted by various dihydroxyl compounds represented by the following formulas:

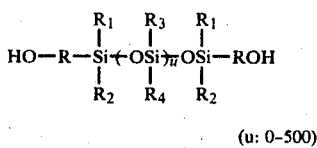

(u: 0-500)

where R is an alkylene group having from 1 to 10 carbon atoms, and each of $R_1$, $R_2$, $R_3$ and $R_4$ is an alkyl or substituted alkyl group having from 1 to 10 carbon atoms.

(b) $HOCH_2Rf'CH_2OH$ where Rf' is $-CH_2-(CF_2)_v-CH_2(v: 1-10)$, $-CH_2CF_2CF_2OCF_2CF_2CH_2-$, $-CH_2CF_2CF_2O(CF_2)_wOCF_2CF_2CH_2-$ (w: 1-5), $-CF(CF_3)O(CF_2)_wOCF(CF_3)-$, $-CH_2CF_2CF_2OCF_2CF(CF_3)O(CF_2)_wOCF(CF_3)CF_2OCF_2CF_2CH_2-$,

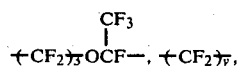

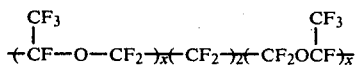

(x: 0-5), etc.

(c) $HOCH_2CH_2OCO(CH_2)_yCOOCH_2CH(CH_3)OH$ (y: 1-5)

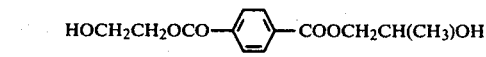  (d)

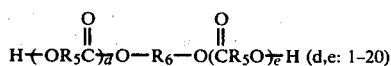  (e)

where $R_5$ is

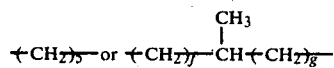

(f+g=4), and $R_6$ is $-(CH_2)_h-$ (h=2, 4, 6), $$-CH_2\overset{CH_3}{\underset{|}{C}}H-, -CH_2CH_2OCH_2CH_2-,$$
$-CH_2CH_2SCH_2CH_2-$, etc.

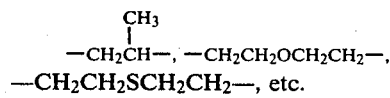  (f)

where $R_7$ is $R_6$,

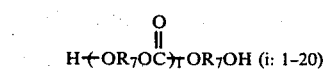, etc.

For instance, if polyorganosiloxane linkages are introduced into A with use of the compounds identified in the above (a), the oxygen permeability, etc. may be improved, whereby the usefulness as a membrane for artificial lungs may be improved, and if fluorine-containing groups are introduced into A with use of the compounds identified in the above (b), the bio-compatibility may further be improved.

As the chain extender for the present invention, various bifunctional compounds such as diamines, diols, dithiols or aromatic dihydroxyl compounds which are reactive with the isocyanate group or the carbamate group may be used. However, diamines are preferably used in view of the durability and mechanical properties of the polymer.

As suitable diamines, there may be mentioned aliphatic diamines such as ethylene diamine, propylene diamine and tetramethylene diamine; aromatic diamines such as xylylene diamine and phenylene diamine; alicyclic diamines such as cyclohexylene diamine; and fluorine-containing diamines such as 2,2,3,3,4,4,-hexafluoropentamethylene diamine.

In the present invention, the operation and conditions for the chain extending reaction are not critical. However, primarily for the removal of the heat generated by the reaction, the reaction is preferably carried out in a solvent, particularly by dropwise adding a chain extender solution to the prepolymer solution. From the practical point of view, it is advantageous to use the same solvent as used for the preparation of the prepolymer. As such a solvent, there may be used various kinds of solvents which are not reactive with the starting materials or products. A non-polar solvent such as a hydrocarbon may be used. However, in view of the solubility of the prepolymer, it is preferred to use a polar solvent. Among polar solvents, relatively volatile ones such as ethyl acetate, butyl acetate or dioxane, are particularly advantageous for the separation of the product from the reaction mixture.

The reaction temperature is preferably from $-10°$ to $200°$ C., especially from $0°$ to $100°$ C. The reaction may be carried out under atmospheric pressure or under elevated pressure.

In view of both the solubility in the solvent and the mechanical properties of the polymer, the molecular weight of the fluorine-containing block polymer of the present invention is preferably such that the inherent viscosity ($\eta$inh) is from 0.1 to 1.5 dl/g, especially from 0.2 to 0.9, as measured at a temperature of 30° C. at a concentration of 0.5 g/dl in dimethyl formamide.

The antithrombogenic material of the present invention may be used not only as an independent material directly formed into a tube, a film, a sheet, a complicatedly shaped article, etc. by extrusion, rolling, casting, dipping or injection molding, but also as a coating material to be applied to various preformed polymer, glass, metal or ceramics articles.

Now, the present invention will be described in further detail with reference to Examples. In each Example, the evaluation of the antithrombogenicity was made in accordance with the method proposed by R. I. Lee and P. D. White [Am. J. Med. Sci., 145, 495(1918)]. Namely, into each of two test tubes having an inner diameter of 10 cm and coated with the fluorine-containing block polymer in a thickness of about 50 μm, 1 ml of fresh blood of a goat was introduced, and after expiration of 3 minutes, one of the test tubes was inclined every 60 minutes and from the time when the blood in the tube became no longer flowable, the other test tube was manipulated in the same manner. The point at which the blood in the test tube no longer flowed even if the test tube were gently and completely inverted was taken as the final point. The time required from the initial introduction of the fresh blood to the final point was taken as the final coagulation time. Further, the test tubes in which the blood coagulation was completed, was subjected to centrifugation, whereupon the colour tone of the upper layer was examined to observe the presence or absence of hemolysis.

The tensile breaking strength and elongation of the fluorine-containing block polymer were measured with respect to a membrane formed by a casting method and having a thickness of about 300 μm, as the test specimen. Further, a small piece of the cast membrane was dyed by dipping it in an aqueous solution of 4% osmic acid overnight, then cooled to −80° C. and cut by a microtome to obtain a thin section. The microphase separated structure of the polymer was examined by a transmission electron microscope using the thin section as a test sample and the domain size was thereby measured.

EXAMPLE 1

Into a three-necked flask having a capacity of 200 ml and equipped with a thermocouple, stirrer and reflux condenser, 8.04 g (7.45 mmol) of polytetramethylene glycol (PTG 200 manufactured by Nippon Polyurethane Kogyo K.K.; average molecular weight: 1079), 45 ml of n-butyl acetate and 4.65 g (14.9 mmol) of 2,2,3,3,4,4,5,5,-octafluorohexamethylene diisocyanate-[OCNCH$_2$(CF$_2$)$_4$CH$_2$NCO] were charged in this order under nitrogen atmosphere, and the mixture was heated and stirred for 3 hours while maintaining the temperature of the solution at 100° C. and it was then cooled to room temperature, whereby a n-butyl acetate solution of a prepolymer having a structure represented by the formula

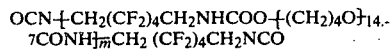

where m is 1, and containing a small amount of the one where m is 2, was obtained.

To the prepolymer solution thus obtained, 0.45 g (7.5 m mol) of ethylene diamine dissolved in 80 ml of n-butyl acetate was dropwise added at a rate to maintain the temperature of the solution at 15° C., under stirring. At the end of the dropwise addition, precipitation of an agar-like polymer was observed. The solution was further stirred at room temperature overnight, and then the solvent was distilled off under reduced pressure. The dried polymer was washed first with ethanol and then with ion-exchanged water, then vacuum dried at 40° C., refined by a reprecipitation method, pulverized by a homogenizer, and again vacuum dried at 40° C. overnight, whereupon 9.48 g (yield: 78%) of a white refined polymer was obtained.

The polymer thus obtained had an inherent viscosity ($\eta$inh) of 0.81 dl/g as measured at 30° C. at a concentration of 0.5 g/dl in N,N-dimethylformamide. The tensile breaking strength and elongation were 630 kg/cm$^2$ and 780%, respectively, as measured with respect to a membrane formed from an N-methylpyrrolidone solution of the polymer by a casting method and having a thickness of about 300 μm. The domain size of the microphase separated structure was about 20 Å. The blood coagulation time as measured by the above mentioned method was 79 minutes. Thus, it was confirmed that the antithrombogenicity was superior to the measured value (13 minutes) with respect to the test tube which was not coated with the polymer or the measured value (20 minutes) with respect to the test tube which was coated with polyvinylchloride. The hemolysis examined at the same time was negative.

EXAMPLES 2 to 4

Various fluorine-containing block polymers were prepared in the same manner as in Example 1 except that instead of ethylene diamine, various other chain extenders were used. The yields and the physical properties of the polymers thus obtained are shown in Table 1. Further, the hemolysis was negative in each of the polymers.

TABLE 1

|  | Example 2*[1] | Example 3 | Example 4 |
|---|---|---|---|
| Chain extender | Phenylene-diamine | FN*[2] | m-xylylene-diamine |
| Yield (%) | 79 | 54 | 64 |
| $\eta$inh (dl/g) | 0.71 | 0.36 | 0.88 |
| Strength (kg/cm$^2$) | 180 | 82 | 590 |
| Elongation (%) | 800 | 890 | 650 |
| Domain size (Å) | 20–80 | about 40 | 40–80 |
| Coagulation time (min.) | 64 | 82 | 64 |

*[1]Synthesized in ethylacetate
*[2]FN: 2,2,3,3,4,4-hexafluoropentamethylenediamine H$_2$NCH$_2$(CF$_2$)$_3$CH$_2$NH$_2$

EXAMPLE 5

The reaction was performed in the same manner as in Example 1 except that the amounts of polytetramethylene glycol, 2,2,3,3,4,4,5,5-octafluorohexamethylenediisocyanate and n-butyl acetate were Lb 10.72 g (9.93 m mol), 4.65 g (14.9 m mol) and 60 ml, respectively, whereby a n-butyl acetate solution of a prepolymer composed mainly of the one having the formula as shown in Example 1 where m is 2, was obtained.

With use of the prepolymer solution thus obtained, a fluorine-containing block polymer was prepared in the same manner as in Example 1. The yield and the physical properties of the polymer thus obtained are as shown below:

Yield: 67%, $\eta$inh: 0.50 dl/g, Strength: 41 kg/cm$^2$,
Elongation: 1130%, Domain size: about 20 Å,
Blood coagulation time: 48 min., Hemolysis: negative

EXAMPLES 6 to 8

Various prepolymer solutions were prepared in the same manner as in Example 1 except that the kind of the diol was varied, and then fluorine-containing block polymers were prepared in the same manner as in Example 1. The yields and the physical properties of the polymers thus obtained are shown in Table 2. Further, the hemolysis was negative in each of the polymers.

TABLE 2

|  | Example 6 | Example 7 | Example 8 | |
|---|---|---|---|---|
| Kind of the diol | PTG | PEG | PTG | FG |
| Average molecular weight | 657 | 920 | 1079 | 454 |
| Amount (g) | 4.90 | 6.86 | 6.43 | 0.68 |
| Yield (%) | 72 | 48 | 65 | |
| $\eta$inh (dl/g) | 0.69 | 0.91 | 0.44 | |
| Strength (kg/cm$^2$) | 300 | 71 | 165 | |
| Elongation (%) | 650 | 1500 | 920 | |
| Domain size (Å) | 20–40 | about 20 | about 20 | |

TABLE 2-continued

|  | Example 6 | Example 7 | Example 8 |
|---|---|---|---|
| Coagulation time (min.) | 78 | 57 | 41 |

PTG: Polytetramethylene glycol
PEG: Polyethylene glycol
FG: Fluorine-containing glycol
(HOCH$_2$CFO(CF$_2$)$_4$OCFCH$_2$OH)
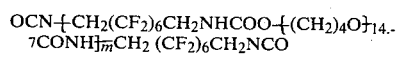
CF$_3$    CF$_3$

EXAMPLE 9

The reaction was performed in the same manner as in Example 1 except that 2,2,3,3,4,4,5,5,6,6,7,7-dodecafluorooctamethylenediisocyanate [OCNCH$_2$(CF$_2$)$_6$CH$_2$NCO] was used as the fluorine-containing diisocyanate, and the amounts of polytetramethylene glycol, the fluorine-containing diidocyanate and n-butyl acetate were 5.54 g (5.14 m mol), 4.35 g (10.6 m mol) and 30 ml, respectively, whereby a n-butyl acetate solution of a prepolymer having a structure represented by the formula OCN─[CH$_2$(CF$_2$)$_6$CH$_2$NHCOO─[(CH$_2$)$_4$O]$_{14.}$$_7$CONH]$_{\overline{m}}$CH$_2$ (CF$_2$)$_6$CH$_2$NCO and composed mainly of the one where m is 1, was obtained. With use of this solution, a fluorine-containing block polymer was prepared in the same manner as Example 1. The yield and the physical properties of the polymer thus obtained were as follows:
Yield: 75%, ηinh: 0.44 dl/g, Strength: 144 kg/cm$^2$
Elongation: 760%, Domain size: about 20 Å,
Blood coagulation time: 86 min., Hemolysis: negative

EXAMPLE 10

The operation was performed in the same manner as in Example 1 except that 9.31 g (7.45 m mol) of a dihydroxyl compound represented by the formula

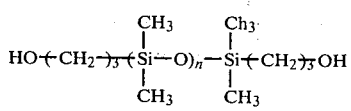

(n=14.5, average molecular weight: 1,250) was used instead of polytetramethylene glycol, and the temperature of the solution at the time of the prepolymer synthesis was kept at 120° C., whereby 10.37 g (yield: 72%) of a white refined polymer was obtained.

The polymer thus obtained had an inherent viscosity (ηinh) of 0.20 dl/g as measured at 30° C. at a concentration of 0.5 g/dl in N,N-dimethylformamide. The oxygen permeability coefficient P(O$_2$) was $28 \times 10^{-9}$ cc·cm/sec·cm$^2$·cmHg, and the carbon dioxide permeability coefficient P(CO$_2$) was $160 \times 10^{-9}$ cc·cm/sec·cm$^2$·cmHg. The blood coagulation time measured by the Lee-White method was 83 minutes.

EXAMPLE 11

The reaction was performed in the same manner as in Example 10 except that the amount of the dihydroxyl compound as used in Example 10 was 4.66 g (3.73 m mol) and the dihydroxyl compound was used as a mixture with 4.02 g (3.73 m mol) of polytetramethylene glycol (PTG 200 manufactured by Nippon Polyurethane Kogyo K.K., average molecular weight: 1,079), whereby 10.47 g (yield; 76%) of a white refined polymer was obtained. Its ηinh was 0.33 dl/g, the tensile breaking strength was 70 kg/cm$^2$, and the elongation was 480%. Further, P(O$_2$) and P(CO$_2$) were $5.7 \times 10^{-9}$ cc·cm/sec·cm$^2$·cmHg and $37 \times 10^{-9}$ cc·cm/sec·cm$^2$·cmHg, respectively. The blood coagulation time was 49 minutes.

EXAMPLES 12 to 14

White refined polymers were obtained in the same manner as in Example 10 except that the ratio of the dihydroxyl compound to PTG 200 was varied. The results thereby obtained are shown in Table 3. Further, in each of Examples 10 to 14, the domain size was about 20 Å and no hemolysis was observed.

TABLE 3

|  | (a):(b) | Yield (%) | ηinh (dl/g) | Gas permeability | | Tensile properties | | Coagulation time (min.) |
|---|---|---|---|---|---|---|---|---|
|  |  |  |  | P(O$_2$) × 10$^9$ (cc.cm/sec.cm$^2$.cmHg) | P(CO$_2$) × 10$^9$ | TB (kg/cm$^2$) | EB (%) |  |
| Example 10 | 1:0 | 72 | 0.20 | 28 | 160 | — | — | 86 |
| 11 | 1:1 | 76 | 0.33 | 5.7 | 37 | 70 | 470 | 49 |
| 12 | 3:1 | 80 | 0.26 | 16 | 97 | 34 | 200 | 54 |
| 13 | 7:1 | 66 | 0.21 | 20 | 116 | — | — | 67 |
| 14 | 1:9 | 70 | 0.59 | 1.3 | 11 | 300 | 670 | 42 |
| Glass | — | — | — | — | — | — | — | 13 |
| Medical silicone | — | — | — | — | — | — | — | 20 |

We claim:

1. An antithrombogenic material which is composed of a fluorine-containing block polymer obtained by the polyaddition or polycondensation of a prepolymer with a chain extender, said prepolymer being a diisocyanate prepolymer represented by the formula OCN─[CH$_2$RfCH$_2$NH─COO─A─CONH]$_{\overline{m}}$CH$_2$RfCH$_2$NCO    (I)

where Rf is a perfluoroalkylene or perfluoroxyalkylene group having from 1 to 20 carbon atoms and containing from 0 to 10 ether linkages, A is a divalent organic group containing an oxygen atom in its main chain and m is from 1 to 3, or a dicarbamate prepolymer obtained by reacting the diisocyanate prepolymer with a lower alcohol.

2. The antithrombogenic material according to claim 1 wherein A is an oxyalkylene group having an average molecular weight of from 40 to 10,000.

3. The antithrombogenic material according to claim 1 wherein the chain extender is a diamine.

* * * * *